United States Patent [19]

Lappi et al.

[11] Patent Number: 6,063,758
[45] Date of Patent: May 16, 2000

[54] SUBSTANCE P-SAPORIN (SP-SAP) CONJUGATES AND METHODS OF USE THEREOF

[75] Inventors: Douglas A. Lappi, Del Mar, Calif.; Ronald G. Wiley, Brentwood, Tenn.

[73] Assignee: Advanced Targeting Systems, Inc., San Diego, Calif.

[21] Appl. No.: 08/890,157

[22] Filed: Jul. 9, 1997

[51] Int. Cl.[7] .............................. A61K 38/00; A61K 38/16
[52] U.S. Cl. ................................. 514/2; 514/13; 530/320; 530/350
[58] Field of Search .......................... 514/2, 13; 530/350, 530/326, 370

[56] References Cited

U.S. PATENT DOCUMENTS 5,191,067   3/1993   Lappi et al. ............................. 530/399
5,679,637  10/1997   Lappi et al. ................................. 514/2

Primary Examiner—Cecilia Tsang
Assistant Examiner—Michael Borin
Attorney, Agent, or Firm—Peter J. Phillips

[57] ABSTRACT

This invention provides a conjugate comprising Substance P, and analogs thereof, and Saporin. This invention provides a method of reducing the perception of pain by a subject comprising administering to the subject an effective dose of the pharmaceutical composition of the conjugate comprising Substance P, and analogs thereof, and Saporin, so as to reduce the perception of pain by the subject. This invention provides a method of selectively destroying NK-1 receptor expressing cells in a subject comprising administering to the subject an effective dose of the conjugate comprising Substance P, and analogs thereof, and Saporin so as to selectively destroy NK-1 receptor expressing cells. Lastly, this invention provides a method for treating a NK-1 receptor associated disorder in a subject, which comprises administering to the subject an amount of the pharmaceutical composition comprising Substance P, and analogs thereof, and Saporin thereby treating the disorder associated with the NK-1 receptor.

9 Claims, 9 Drawing Sheets

FIG. 9A

N⬡-S-S-CH$_2$-CH$_2$-C(=O)-O-N-SAP + HS-CYGGGGGG-SP

→ SP-SAP + N⬡-SH

Reporter molecule
(absorbs at 343 nM)

FIG. 9B

N⬡-S-S-CH$_2$-CH$_2$-C(=O)-O-N-SAP + (CYGGGGGG)-[Sar$^9$, M(O$_2$)$^{11}$]SP

→ [Sar$^9$, M(O$_2$)$^{11}$]SP-SAP + N⬡-SH

FIG. 9C

N⬡-S-S—HS-CYGGGGGG-SP + recombinant HS-Cys$^{-1}$-SAP

→ SP-SAP + N⬡-SH

FIG. 9D

N⬡-S-S—(CYGGGGGG)-[Sar$^9$, M(O$_2$)$^{11}$]SP + recombinant HS-Cys$^{-1}$-SAP

→ [Sar$^9$, M(O$_2$)$^{11}$]SP-SAP + N⬡-SH

FIG. 9E a recombinant form of saporin and substance P expressed in a recombinant protein expression system with the sequence of saporin, an appropriate linker and substance P that terminates with an additional glycine after Met$^{11}$. The purified expressed protein is then converted to the amide with an appropriate enzyme, e.g., peptidylglycine-a-amidating monooxygenase

SUBSTANCE P-SAPORIN (SP-SAP) CONJUGATES AND METHODS OF USE THEREOF

Throughout this application, various publications may be referenced by Arabic numerals in parenthesis. Full citations for these publications may be found at the end of the Detailed Description of the Invention. The disclosures of all publications cited herein are in their entirety hereby incorporated by reference into this application to more fully describe the state of the art to which this invention pertains.

BACKGROUND OF THE INVENTION

Many neurons synthesize and secrete small peptides that act on specific postsynaptic receptors and modify the activity of target neurons. Specific receptor molecules have been identified by binding studies and in some cases, such as the neurokinin-1 receptor (NK-1R) for Substance P (SP), the receptor has been cloned and sequenced. The NK-1R is found in many locations thought to be postsynaptic to SP-secreting terminals such as the cortical nucleus of the amygdala, striatum, locus coeruleus, rostral half of the nucleus ambiguous, nucleus tractus solitarius, dorsal motor nucleus of the vagus, intermediolateral cell column and lamina I and III of the dorsal horn of the spinal cord (1,2). Studies with agonists and antagonists indicate that most, if not all, of the effects of SP in the mammalian CNS are attributable to action at the G-protein coupled NK-1R (3).

A number of functional roles have been attributed to SP in keeping with anatomical studies (e.g. (3)) that show neurons expressing SP in a number of locations throughout the CNS, PNS and gut. For example, experiments utilizing injections of SP into the lateral ventricles have shown increases in blood pressure and heart rate as well as stereotyped behaviors such as face washing, grooming, and wet dog shakes (3). These autonomic manifestations are likely attributable to action in the medulla where prominent NK-1R expression has been demonstrated in the nucleus tractus solitarius, and stereotyped behaviors may reflect action in the basal ganglia and/or limbic system (1,4–6). The current state of knowledge, however, does not unambiguously identify the site of action for these and many other effects of SP. All of these actions are likely mediated through action of substance P at NK-1R (3,4).

The best known role for SP is in nociception. Small unmyelinated C-fibers of the peripheral nervous system that are thought to be primary nociceptive neurons secrete SP and glutamate. Capsaicin, an agent that can destroy C-fibers, produces cutaneous analgesia and is approved for topical use to alleviate the pain of postherpetic neuralgia (Zostrix). Capsaicin injection of neonates has long been used to produce animals with no C-fibers and altered threshold to painful cutaneous stimuli. SP-containing nerve terminals are present in the spinal nucleus of the trigeminal nerve and the superficial layers of the spinal dorsal horn, areas known to be important in pain perception (1) and rich in NK-1R (1,2). In spite of the development of peptide and nonpeptide antagonists of NK-1R, considerable controversy remains about the precise role of SP acting at NK-1R in pain perception (7–17).

SUMMARY OF THE INVENTION

This invention provides conjugates comprising Substance P, and analogs thereof, and Saporin (SAP).

This invention provides a method of reducing the perception of pain by a subject comprising administering to the subject an effective amount of the pharmaceutical composition of the conjugate comprising Substance P, and analogs thereof, and Saporin, so as to reduce the perception of pain by the subject.

This invention provides a method of selectively destroying NK-1 receptor expressing cells in a subject comprising administering to the subject an effective amount of the conjugate comprising Substance P, and analogs thereof, and Saporin so as to selectively destroy NK-1 receptor expressing cells.

Lastly, this invention provides a method for treating a NK-1 receptor associated disorder in a subject, which comprises administering to the subject an amount of the pharmaceutical composition comprising Substance P, and analogs thereof, and Saporin thereby treating a disorder associated with the NK-1 receptor.

BRIEF DESCRIPTION OF THE FIGURES

FIGS. 8A–9D: In vivo effects of SSP-SAP in rats.

FIGS. 9A–9E: Synthesis of Substance P- Saporin, (SEQ ID Nos. 3 and 4).

DETAILED DESCRIPTION OF THE INVENTION

Figure 1:
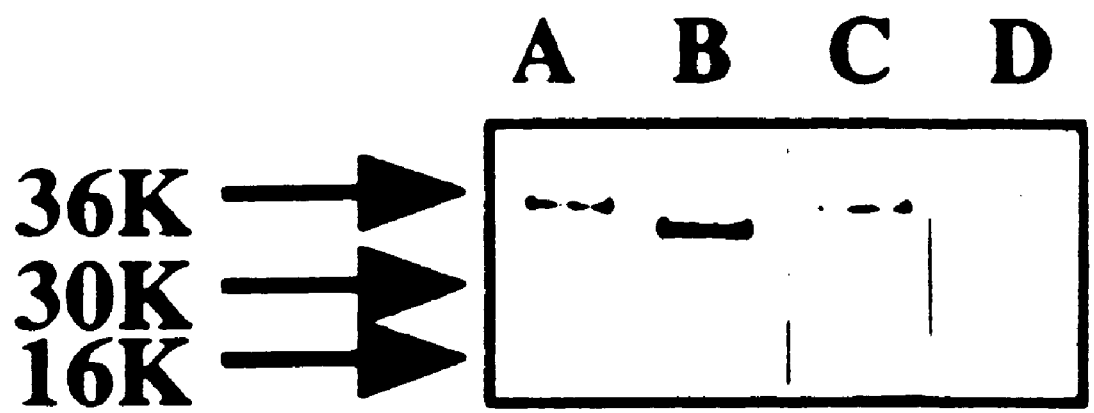
FIG. 1: Sodium dodecyl sulfate polyacrylamide gel electrophoresis of NTE-SP-SAP.

This invention provides a conjugate comprising Substance P and Saporin (SP-SAP). In one embodiment the conjugate comprises an analog of Substance P. In another embodiment the conjugate comprises an analog of Saporin.

This invention provides a conjugate comprising a Substance P analog having the amino acid sequence CYGGGGGGGRPKPQQFFSarLMet($O_2$)-amide (SEQ ID No. 1) and Saporin (SSP-SAP). This invention provides a conjugate comprising a Substance P analog having the amino acid sequence at the N-terminus CYGGGGGGGRPKPQQFFGLM-amide (SEQ ID No. 2) and Saporin (NTE-SAP).

This invention provides a conjugate comprising Substance P and a ribosome-inactivating protein.

This invention provides a conjugate comprising a Substance P analog having the amino acid sequence CYGGGGGGGRPKPQQFFSarLMet($O_2$)-amide and a ribosome-inactivating protein. In one embodiment the ribosome-inactivating protein is ricin A chain, gelonin, pokeweed antiviral protein, diphtheria toxin or pseudomonas aeruginosa toxin or fragments thereof.

This invention provides a conjugate comprising a Substance P analog having the amino acid sequence CYGGGGGGGRPKPQQFFGLM-amide and a ribosome-inactivating protein. In one embodiment the ribosome-inactivating protein is ricin A chain, gelonin, pokeweed antiviral protein, diphtheria toxin or pseudomonas aeruginosa toxin or fragments thereof.

Substance P can be attached to Saporin through a chemical bond, or the composition can be prepared as a chimera using techniques of recombinant DNA. The conjugate can be used to treat Substance P, or an analog thereof, mediated pathophysiological conditions by specifically targeting cells having Substance P, or an analog thereof, receptors and inhibiting proliferation of or causing death of such cells. Additionally, the conjugate can be used to target cytotoxic agents into cells having Substance P, or an analog thereof, receptors to inhibit the proliferation of such cells. Saporin and Saporin derivatives are known to the skilled in the art. Saporin is a potent ribosome inactivating protein (RIP) which is isolated from the seeds of the plant Saponaria officinalis (see Stirpe, et al., Biochem. J., 216:617–625 (1983)).

This invention provides a fusion protein comprising the amino acid sequence encoding Substance P and Saporin. This invention provides a recombinant nucleic acid molecule comprising an isolated nucleic acid molecule encoding Substance P and Saporin.

In one embodiment Saporin is conjugated to an agent. Such agents include but are not limited to the following: alkaline phosphatase, beta- galactosidase, glucose-6-phosphate dehydrogenase, maleate dehydrogenase and peroxidase, chemiluminescent agents which include luminol, isoluminol, aromatic acridinium esters, imidazoles, acridinium salts, and oxalate esters. Similarly, bioluminescent compounds may be utilized for labeling, the bioluminescent compounds including luciferin, luciferase, and aequorin.

In another embodiment Saporin is conjugated to an antibody. An antibody, polypeptide or isolated nucleic acid molecule may be labeled with a detectable marker including, but not limited to: a radioactive label, or a colorimetric, a luminescent, or a fluorescent marker, or gold. Radioactive labels include, but are not limited to: $^3H$, $^{14}C$, $^{32}P$, $^{33}P$, $^{35}S$, $^{36}Cl$, $^{51}Cr$, $^{57}Co$, $^{59}Co$, $^{59}Fe$, $^{90}Y$, $^{125}I$, $^{131}I$, and $^{186}Re$. Fluorescent markers include, but are not limited to: fluorescein, rhodamine and auramine. Colorimetric markers include, but are not limited to: biotin, and digoxigenin. Further, the antibody, polypeptide or nucleic acid molecule may be detected by a second antibody that may be linked to an enzyme, such as alkaline phosphatase or horseradish peroxidase. Other enzymes which may be employed are well known to one of ordinary skill in the art.

Antibodies or antibody fragments that would be useful would be antibodies to the NK-1 receptor. Antibody fragments useful in the present invention include F(ab')2, F(ab)2, Fab', Fab, Fv and the like including hybrid fragments. Preferred fragments are Fab', F(ab')2, Fab, and F(ab)2. Also useful are any subfragments retaining the hypervariable, antigen-binding region of an immunoglobulin and having a size similar to or smaller than a Fab' fragment. This will include genetically engineered and/or recombinant proteins, whether single-chain or multiple-chain, that incorporate an antigen binding site and otherwise function in vivo as targeting vehicles in substantially the same way as natural immunoglobulin fragments. Fab' antibody fragments may be conveniently made by reductive cleavage of F(ab')2 fragments, which themselves may be made by pepsin digestion of intact immunoglobulin. Fab antibody fragments may be made by papain digestion of intact immunoglobulin, under reducing conditions, or by cleavage of F(ab)2 fragments which result from careful papain digestion of whole immunoglobulin. The fragments may also be produced by genetic engineering.

Antibodies against tumor antigens and against pathogens are known. For example, antibodies and antibody fragments which specifically bind markers produced by or associated with tumors or infectious lesions, including viral, bacterial, fungal and parasitic infections, and antigens and products associated with such microorganisms. In particular, antibodies against an antigen, e.g., a gastrointestinal, lung, breast, prostate, ovarian, testicular, brain or lymphatic tumor, a sarcoma or a melanoma, are advantageously used.

This invention provides a pharmaceutical composition comprising a therapeutically effective amount of the conjugate comprising Substance P and Saporin (SP-SAP) and a pharmaceutically acceptable carrier.

This invention provides a pharmaceutical composition comprising a therapeutically effective amount of the conjugate comprising a Substance P analog having the amino acid sequence CYGGGGGGGRPKPQQFFSarLMet(O$_2$)-amide and Saporin (SSP-SAP) (SEQ ID NO:1) and a pharmaceutically acceptable carrier.

This invention provides a pharmaceutical composition comprising a therapeutically effective amount of the conjugate comprising a Substance P analog having the amino acid sequence CYGGGGGGGRPKPQQFFGLM-amide (SEQ ID No. 2) and Saporin (NTE-SAP) and a pharmaceutically acceptable carrier.

This invention provides a pharmaceutical composition comprising a therapeutically effective amount of the conjugate comprising a Substance P and a ribosome-inactivating protein and a pharmaceutically acceptable carrier.

This invention provides a pharmaceutical composition comprising a therapeutically effective amount of the conjugate comprising a Substance P analog having the amino acid sequence CYGGGGGGGRPKPQQFFSarLMet(O$_2$)-amide (SEQ ID No. 1) and a ribosome-inactivating protein and a pharmaceutically acceptable carrier. In one embodiment the ribosome-inactivating protein is ricin A chain, gelonin, pokeweed antiviral protein, diphtheria toxin or pseudomonas aeruginosa toxin or fragments thereof.

This invention provides a pharmaceutical composition comprising a therapeutically effective amount of the conjugate comprising a Substance P analog having the amino acid sequence CYGGGGGGGRPKPQQFFGLM-amide (SEQ ID No. 2) and a ribosome-inactivating protein and a pharmaceutically acceptable carrier. In one embodiment the ribosome-inactivating protein is ricin A chain, gelonin, pokeweed antiviral protein, diphtheria toxin or pseudomonas aeruginosa toxin or fragments thereof.

In one embodiment the pharmaceutical composition further comprises a cytokine. Examples of cytokines include but are not limited: transforming growth factor beta, epidermal growth factor family, fibroblast growth factors, hepatocyte growth factor, insulin-like growth factors, B-nerve growth factor, platelet-derived growth factor, vascular endothelial growth factor, interleukin 1, IL-1 receptor antagonist, interleukin 2, interleukin 3, interleukin 4, interleukin 5, interleukin 6, IL-6 soluble receptor, interleukin 7, interleukin 8, interleukin 9, interleukin 10, interleukin 11, interleukin 12, interleukin 13, angiogenin, chemokines, colony stimulating factors, granulocyte-macrophage colony stimulating factors, erythropoietin, interferon, interferon gamma, leukemia inhibitory factor, oncostatin M, pleiotrophin, secretory leukocyte protease inhibitor, stem cell factor, tumor necrosis factors, and soluble TNF receptors.

This invention provides a method of reducing/alleviating/decreasing the perception of pain by a subject comprising administering to the subject an effective amount of the pharmaceutical composition comprising a therapeutically effective amount of the conjugate comprising Substance P and Saporin (SP-SAP) and a pharmaceutically acceptable carrier so as to reduce the perception of pain by the subject.

This invention provides a method of reducing the perception of pain by a subject comprising administering to the subject an effective amount of the pharmaceutical composition comprising a therapeutically effective amount of the conjugate comprising a Substance P analog which has the amino acid sequence CYGGGGGGGRPKPQQFFSarLMet(O$_2$)-amide (SEQ ID No. 1) and Saporin (SSP-SAP) and a pharmaceutically acceptable carrier so as to reduce the perception of pain by the subject.

This invention provides a method of reducing the perception of pain by a subject comprising administering to the subject an effective amount of the pharmaceutical composition comprising a therapeutically effective amount of the conjugate comprising a Substance P analog which has the amino acid sequence CYGGGGGGGRPKPQQFFGLM-amide (SEQ ID No. 2) and Saporin (NTE-SAP) and a pharmaceutically acceptable carrier so as to reduce the perception of pain by the subject.

This invention provides a method of reducing the perception of pain by a subject comprising administering to the subject an effective amount of the pharmaceutical composition comprising a therapeutically effective amount of the conjugate comprising a Substance P analog which has the amino acid sequence CYGGGGGGGRPKPQQFFSarLMet(O$_2$)-amide (SEQ ID No. 1) and a ribosome-inactivating protein and a pharmaceutically acceptable carrier so as to reduce the perception of pain by the subject.

This invention provides a method of reducing the perception of pain by a subject comprising administering to the subject an effective amount of the pharmaceutical composition comprising a therapeutically effective amount of the conjugate comprising a Substance P analog which has the amino acid sequence CYGGGGGGGRPKPQQFFGLM-amide (SEQ ID No: 2) and a ribosome-inactivating protein and a pharmaceutically acceptable carrier so as to reduce the perception of pain by the subject.

This invention provides a method of reducing the perception of pain by a subject comprising administering to the subject an effective amount of the pharmaceutical composition comprising a therapeutically effective amount of the conjugate comprising Substance P and a ribosome-inactivating protein and a pharmaceutically acceptable carrier so as to reduce the perception of pain by the subject. In one embodiment the ribosome-inactivating protein is ricin A chain, gelonin, pokeweed antiviral protein, diphtheria toxin, pseudomonas aeruginosa toxin or fragments thereof.

This invention provides conjugates of Substance P and analogs of Saporin. For example, analogs of Saporin include but are not limited to Cys-1SAP, and Gly-SAP. An analog according to the present invention may be an analog of gelonin. An analog according to the present invention may be an analog of barley ribosome-inactivating protein. An analog according to the present invention may be an analog of momordin II. The present invention also provides a polynucleotide encoding an analog of a Type I ribosome-inactivating protein. The present invention also provides an agent toxic to a cell including an analog of a Type I ribosome-inactivating protein linked by a disulfide bond through a cysteine to a molecule which specifically binds to the cell, which cysteine is at an amino acid position in the analog.

Substance P, or an analog thereof, Saporin conjugates can be used to target the cytotoxic agent to cells expressing Substance P, or an analog thereof, receptors in order to cause cell death.

This invention provides a method of selectively destroying NK-1 receptor expressing cells in a subject comprising administering to the subject an effective amount of the pharmaceutical composition comprising a therapeutically effective amount of the conjugate comprising Substance P and Saporin and a pharmaceutically acceptable carrier so as to selectively destroy NK-1 receptor expressing cells.

This invention provides a method of selectively destroying NK-1 receptor expressing cells in a subject comprising administering to the subject an effective amount of the pharmaceutical composition comprising a therapeutically effective amount of the conjugate comprising Substance P analogs SSP-SAP or NTE-SAP and Saporin and a pharmaceutically acceptable carrier so as to selectively destroy NK-1 receptor expressing cells.

This invention provides a method of selectively destroying NK-1 receptor expressing cells in a subject comprising administering to the subject an effective amount of the pharmaceutical composition comprising a therapeutically effective amount of the conjugate comprising Substance P analogs SSP-SAP or NTE-SAP and a ribosome-inactivating protein and a pharmaceutically acceptable carrier so as to selectively destroy NK-1 receptor expressing cells. In one embodiment the ribosome-inactivating protein is ricin A chain, gelonin, pokeweed antiviral protein, diphtheria toxin, pseudomonas aeruginosa toxin or fragments thereof.

This invention provides a method of treating a subject with cancer comprising administering to the subject an effective amount of the pharmaceutical composition comprising a therapeutically effective amount of the conjugate comprising Substance P and Saporin and a pharmaceutically acceptable carrier so as to treat the cancer.

This invention provides a method of treating a subject with cancer comprising administering to the subject an effective amount of the pharmaceutical composition comprising a therapeutically effective amount of the conjugate comprising Substance P analogs SSP-SAP or NTE-SAP and Saporin and a pharmaceutically acceptable carrier so as to treat the cancer.

This invention provides a method of treating a subject with cancer comprising administering to the subject an effective amount of the pharmaceutical composition comprising a therapeutically effective amount of the conjugate comprising Substance P analogs SSP-SAP or NTE-SAP and a ribosome-inactivating protein and a pharmaceutically acceptable carrier so as to treat the cancer. In one embodiment the ribosome-inactivating protein is ricin A chain, gelonin, pokeweed antiviral protein, diphtheria toxin, pseudomonas aeruginosa toxin or fragments thereof.

This invention provides a method for treating a NK-1 receptor associated disorder in a subject, which comprises administering to the subject an amount of the pharmaceutical composition comprising a therapeutically effective amount of the conjugate comprising Substance P and Saporin and a pharmaceutically acceptable carrier thereby treating the disorder associated with the NK-1 receptor.

This invention provides a method for treating a NK-1 receptor associated disorder in a subject, which comprises administering to the subject an amount of the pharmaceutical composition comprising a therapeutically effective amount of the conjugate comprising Substance P analogs SSP-SAP or NTE-SAP and Saporin and a pharmaceutically acceptable carrier thereby treating the disorder associated with the NK-1 receptor.

This invention provides a method for treating a NK-1 receptor associated disorder in a subject, which comprises administering to the subject an amount of the pharmaceutical composition comprising a therapeutically effective amount of the conjugate comprising Substance P analogs SSP-SAP or NTE-SAP and a ribosome-inactivating protein and a pharmaceutically acceptable carrier thereby treating the disorder associated with the NK-1 receptor. In one embodiment the ribosome-inactivating protein is ricin A chain, gelonin, pokeweed antiviral protein, diphtheria toxin, pseudomonas aeruginosa toxin or fragments thereof These disorders or diseases include but are not limited to: respiratory conditions (e.g. asthma, allergic rhinitis), ophthalmic conditions (e.g. conjunctivitis), cutaneous conditions (e.g. allergic dermatitis, dermatitis by contact, psoriasis), intestinal conditions (e.g. ulcerative colitis, Crohn's disease), gastrointestinal tract, central nervous system disorders such as anxiety and psychosis, inflammatory diseases such as rheumatoid arthritis and inflammatory bowel diseases, as well as pain in any of the aforesaid conditions, including migraine.

Other disorders or diseases include but are not limited to: Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases, proliferative vitreoretinopathy, irritable bowel syndrome and disorders of bladder function including cystitis and bladder detrusor hyperreflexia, demyelinating diseases such as multiple sclerosis and amyotrophic lateral sclerosis, asthmatic disease, small cell carcinomas, in particular small cell lung cancer, depression, dysthymic disorders, chronic obstructive airways disease, hypersensitivity disorders such as poison ivy, vasospastic diseases such as angina and Reynauld's disease, fibrosing and collagen diseases such as scleroderma and eosinophilic fascioliasis, reflex sympathetic dystrophy such as shoulder/hand syndrome, addiction disorders such as alcoholism, stress related somatic disorders, neuropathy, neuralgia, disorder related to immune enhancement or suppression such as systemic lupus erythmatosis conjunctivitis, vernal conjunctivitis, contact dermatitis, atopic dermatitis, urticaria, and other eczematoid dermatitis and emesis; central nervous system disorders such as anxiety, depression, psychosis and schizophrenia; neurodegenerative disorders such as AIDS related dementia, senile dementia of the Alzheimer type, Alzheimer's disease and Down's syndrome; demyelinating diseases such as multiple sclerosis (MS) and amyotrophic lateral sclerosis (ALS; Lou Gehrig's disease) and other neuropathological disorders such as peripheral neuropathy, inflammatory diseases such as inflammatory bowel disease, irritable bowel syndrome, psoriasis, fibrositis, ocular inflammation, osteoarthritis and rheumatoid arthritis; allergies such as eczema and rhinitis; hypersensitivity disorders such as poison ivy; ophthalmic diseases such as conjunctivitis, vernal conjunctivitis, dry eye syndrome, and the like; cutaneous diseases such as contact dermatitis, atopic dermatitis, urticaria, and other eczematoid dermatitis; oedema, such as oedema caused by thermal injury; addiction disorders such as alcoholism; stress related somatic disorders; reflex sympathetic dystrophy such as shoulder/hand syndrome; dysthymic disorders; neuropathy, such as diabetic or peripheral neuropathy and chemotherapy-induced nemopathy; postherpetic and other neuralgias; asthma; osteoarthritis; rheumatoid arthritis; and especially migraine.

The subjects to be treated or whose tissue may be used herein may be a mammal, or more specifically a human, horse, pig, rabbit, dog, cat, monkey, or rodent. In the preferred embodiment the subject is a human.

The invention includes the pharmaceutically acceptable salts and complexes of all the compounds described herein. The salts include but are not limited to the following acids and bases. Examples of suitable inorganic acids include, but are not limited to, hydrochloric acid, hydrofluoric acid, hydrobromic acid, hydroiodic acid, sulfuric acid and boric acid. Examples of suitable organic acids include but are not limited to acetic acid, trifluoroacetic acid, formic acid, oxalic acid, malonic acid, succinic acid, tartaric acid, maleic acid, fumaric acid, methanesulfonic acid, trifluoromethanesulfonic acid, benzoic acid, glycolic acid, lactic acid, citric acid and mandelic acid. Examples of suitable inorganic bases include, but are not limited to, ammonia, hydroxyethylamine and hydrazine. Examples of suitable organic bases include, but are not limited to, methylamine, ethylamine, trimethylamine, triethylamine, ethylenediamine, hydroxyethylamine, morpholine, piperazine and guanidine. The invention further provides for the hydrates and polymorphs of all of the compounds described herein.

In one preferred embodiment, the pharmaceutical carrier may be a liquid and the pharmaceutical composition would be in the form of a solution. In another equally preferred embodiment, the pharmaceutically acceptable carrier is a solid and the pharmaceutical composition is in the form of a powder or tablet. In a further embodiment, the pharmaceutical carrier is a gel and the pharmaceutical composition is in the form of a suppository or cream. In a further embodiment, the compound may be formulated as part of a pharmaceutically acceptable transdermal patch.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for examples, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both, or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant, which are useful for intranasal administration.

Liquid pharmaceutical compositions which are sterile solutions or suspensions can be utilized for intramuscular, intrathecal, intratracheal, epidural, intraperitoneal or subcutaneous injections. Sterile solutions can also be administered intravenously. The compounds may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes and coatings.

The compound can be administered orally in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

The compound can also be administered orally either in liquid or solid composition form. Compositions suitable for oral administration include solid forms such as pills, capsules, granules, tablets and powders, and liquid forms such as solutions, syrups, elixirs and suspensions. Forms useful for parenteral administration include sterile solutions, emulsions and suspensions.

Examples of suitable pharmaceutical carriers include any of the standard pharmaceutically accepted carriers known to those of ordinary skill in the art. Examples of such pharmaceutical carriers include, but are not limited to, phosphate buffered saline solution, water, emulsions such as oil/water emulsions or a triglyceride emulsion, various types of wetting agents, tablets, coated tablets and capsules. A suitable pharmaceutically acceptable carrier may be selected taking into account the chosen mode of administration.

Besides containing an effective amount of the compounds described herein the pharmaceutical compositions may also include suitable diluents, preservatives, solubilizers, emulsifiers, adjuvant and/or carriers.

The resulting pharmaceutical compositions may be liquids or lyophilized or otherwise dried formulations. Examples of suitable diluents include, but are not limited to, Tris-HCL, Tris-acetate and Tris-phosphate. The diluents employed may vary in their buffer content, pH and/or ionic strength. Examples of representative additives which may be used in the present invention include, but are not limited to, albumin or gelatin to prevent absorption to surfaces, detergents (e.g., Tween 20, Tween 80, Pluronic F68, bile acid salts), solubilizing agents (e.g., Thimerosal, benzyl alcohol), bulking substances or tonicity modifiers (e.g., lactose, mannitol), covalent attachment of polymers such as polyethylene glycol to the protein, complexation with metal ions, or incorporation of the material into or onto particulate preparation of polymeric compounds such as polylactic acid, polyglycolic acid, polyvinyl pyrrolidone, etc. or into liposomes, microemulsions, micelles, unilamellar or multimellar vesicles, erythrocyte ghosts, or spheroplasts. Such compositions will influence the physical state, solubility, stability, rate of in vivo release, and rate of in vivo clearance of the compounds.

Examples of optional ingredients which may be included in the pharmaceutical compositions of the present invention include antioxidants, e.g., ascorbic acid; low molecular weight (less than about ten residues) polypeptides, i.e., polyarginine or tripeptide; proteins, such as serum albumin, gelatin, or immunoglobulins; amino acids, such as glycine, glutamine acid, aspartic acid, or arginine; chelating agents such as EDTA; and sugar alcohols such as mannitol or sorbitol.

The choice of composition will depend on the physical and chemical properties of the compounds. Controlled or sustained release compositions include formulation of lipohilic depots (e.g., fatty acids, waxes, oils). Also comprehended by the invention are particulate compositions coated with polymers (e.g., poloxamers or poloxamines) and compounds coupled to antibodies directed against tissue-specific receptors, ligands or antigens or coupled to ligands of tissue-specific receptors. Other embodiments of the compositions of the invention incorporate particulate forms of protective coatings, protease inhibitors or permeation enhancers for various routes of administration, including parenteral, pulmonary nasal and oral.

Suitable topical formulations include gels, creams, solutions, emulsions, carbohydrate polymers, biodegradable matrices thereof, vapors, mists, aerosols, or other inhalants. The compounds of the present invention may be encapsulated in a wafer, wax, film or solid carrier, including chewing gums. Permeation enhancers to aid in transport to movement across the epithelial layer are also known in the art and include, but are not limited to, dimethyl sulfoxide and glycols.

Optimal dosages to be administered may be determined by those skilled in the art, and will vary with the particular compound in use, the strength of the preparation, the mode of administration, and the advancement of the disease condition. Additional factors depending on the particular subject being treated, including subject age, weight, gender, diet, and time of administration, will result in a need to adjust dosages. Administration of the compound may be effected continuously or intermittently.

In any treatment regimen, the composition may be administered to a patient either singly or in a cocktail containing two or more targeted toxins, other therapeutic agents, compositions, or the like, including, but not limited to, immunosuppressive agents, tolerance-inducing agents, potentiators and side-effect relieving agents. Particularly preferred are immunosuppressive agents useful in suppressing allergic reactions of a host. Preferred immunosuppressive agents include prednisone, prednisolone, DECADRON (Merck, Sharp & Dohme, West Point, Pa.), cyclophosphamide, cyclosporine, 6-mercaptopurine, methotrexate, azathioprine and i.v. gamma globulin or their combination. Preferred potentiators include monensin, ammonium chloride, perhexiline, verapamil, amantadine and chloroquine. All of these agents are administered in generally-accepted efficacious dose ranges such as those disclosed in the Physician's Desk Reference, 41st Ed., Publisher Edward R. Barnhart, N.J. (1987).

In the treatment, an appropriate dosage level will generally be about 0.001 to 50 mg per kg patient body weight per day which can be administered in single or multiple doses.

Preferably, the dosage level will be about 0.005 to about 25 mg/kg per day; more preferably about 0.01 to about 10 mg/kg per day; and even more preferably about 0.05 to about 1 mg/kg per day.

This invention is further illustrated in the Experimental Details Sections which follow. These sections are set forth to aid in understanding the invention but are not intended to, and should not be construed to, limit in any way the invention as set forth in the claims which follow thereafter.

Experimental Details Section

Development of a way to selectively destroy the NK-1R expressing neurons not only would greatly enhance our understanding of the role of these neurons and SP in nociception, but also would reveal new approaches to the management of chronic, intractable pain. Similarly, selective lesioning of NK-1R expressing neurons in the basal ganglia, medullary autonomic centers, the limbic system or gut would provide novel and useful information that would further our understanding of the function of SP in these locations as well as lead to possible therapeutic strategies. Moreover, the availability of specific, reversible antagonists and agonists for NK-1R and NK-3R would complement lesions made by a specific cytotoxin, and allow comparison of acute/reversible vs. chronic/irreversible impairment of NK-1R neuron activation. The advantages of NK-1R lesions would result from their long-term effects that would permit detailed physiological, neurochemical and behavioral analyses of changes produced by selective loss of NK-1R+ neurons. The short acting, reversible antagonists will be available to confirm or validate the findings obtained with SP-SAP lesions, an important advantage when developing a novel experimental approach.

Cytotoxins that are specific for NK-1 receptor-bearing cells were made. These cytotoxins are produced by conjugation of SP or [Sar9,Met(O2)11]-SP (SSP), an agonist of SP, to saporin (SAP), a potent ribosome-inactivating protein. SP or its agonist bind to NK-1R, the conjugate is internalized, and SAP inactivates the neuronal protein synthesis mechanism, which results in cell death. The results indicate that spinal intrathecal injections of substance P-saporin (SP-SAP) or $Sar^9Met(O_2)^{11}$-substance P-saporin (SSP-SAP) can be used to lesion NK-1R expressing neurons of the dorsal horn, and suggest that this lesion may decrease pain perception.

Synthesis of SP-SAP and SSP-SAP: An N-terminal-extended form of SP was synthesized (Bio-Synthesis, Inc., Lewisville Tex.): CYGGGGGGRPKPQQFFGLM-amide (SEQ ID No:2) (NTE-SP) or CYGGGGGG-RPKPQQFFSarLMet(O2)-amide (SSP) (SEQ ID No. 1). These analogs keep the C-terminal intact, as is required for SP activity; N-terminal modification is allowed (18). The N-terminal Cys possesses the free sulfhydryl which is able to react with pyridyl dithione-derivatized SAP. This creates a disulfide linkage which has been thought to be necessary in toxin conjugates (19). Saporin was derivatized with N-succinimidyl-3-[2-pyridyldithio]proprionate (SPDP) (20). The reaction product is heterogeneous, with a mixture of zero, one, two and three pyridyl dithio groups attached to SAP under the conditions used. As seen in Table 1, mono-derivatized SAP was able to be purified by the protocol in reference (20).

TABLE 1

Analysis of chromatographic fractions from ion-exchange purification of mono-derivatized saporin.

| fraction number | protein concentration ($\mu$M) | pyridyl thione (PT) ($\mu$M) | ratio protein/PT |
|---|---|---|---|
| 48 | 6.5 | 10.9 | 1.7 |
| 49 | 9.7 | 14.9 | 1.5 |
| 50 | 12.6 | 17.6 | 1.4 |
| 51 | 13.2 | 17.6 | 1.3 |
| 52 | 12.6 | 18.7 | 1.5 |
| 53 | 12.2 | 17.4 | 1.4 |
| 54 | 16.6 | 17.9 | 1.1 |
| 55 | 19.5 | 19.7 | 1.0 |
| 56 | 26.3 | 22.3 | 0.85 |
| 57 | 28.6 | 26.0 | 0.91 |
| 58 | 35.7 | 26.7 | 0.74 |
| 59 | 35.9 | 27.1 | 0.75 |
| 60 | 40.7 | 29.8 | 0.73 |
| 61 | 36.8 | 27.1 | 0.74 |
| 62 | 34.2 | 22.3 | 0.65 |
| 63 | 28.6 | 16.8 | 0,59 |
| 64 | 27.1 | 11.8 | 0.43 |
| 65 | 27.1 | 5.7 | 0.21 |
| 66 | 31.1 | 1.5 | 0.05 |
| pool 56–61 | 32.0 | 32.1 | 1.0 |

A five-fold excess of NTE-SP or SSP was added to the mono-derivatized SAP. Within 20 minutes, the reaction has gone to completion, as determined by pyridyl thiol release. Excess NTE-SP or SSP is removed by extensive dialysis. Subsequent analysis by sodium dodecyl sulfate polyacrylamide gel electrophoresis (SDS-PAGE) and Western blotting determined that the resulting product was a single molecule of NTE-SP or SSP linked to a single SAP through a disulfide linkage (FIGS. 1 and 2).

Electrophoresis was performed with 16% Tricine gels in a mini-gel system (Bio-Rad, Richmond Calif.) according to the manufacturer's instructions. Transfer to nitrocellulose was performed with a Trans-Blot SD Semi-Dry Transfer Cell (Bio-Rad). Staining was as described (21). NTE-SP-SAP (SP-SAP) was electrophoresed and the migration was compared to that of SAP. In FIG. 1, Lanes A and B are stained with Coomassie staining; lanes C and D are from Western blots using anti-SP. A) SP-SAP, B) SAP, C) SP-SAP, D) SP-SAP under reducing conditions. The migration of SP-SAP shows a single band with a slight increase in the molecular weight, accounted for by the molecular weight of the 18 amino acid peptide used for the conjugation. No free SAP is evident, nor any evidence of more than one NTE-SP per molecule of SAP. The Western blotting of the conjugate with an anti-SP antibody indicates that the higher molecular weight species contains SP. The staining is removed upon reduction of the conjugate, indicating that the NTE-SP is linked to SAP by a disulfide bond, as planned. While the molecular weight of SAP is 30,000, its migration in SDS-PAGE is aberrant because its high isoelectric point compromises binding with SDS (22).

Figure 2:
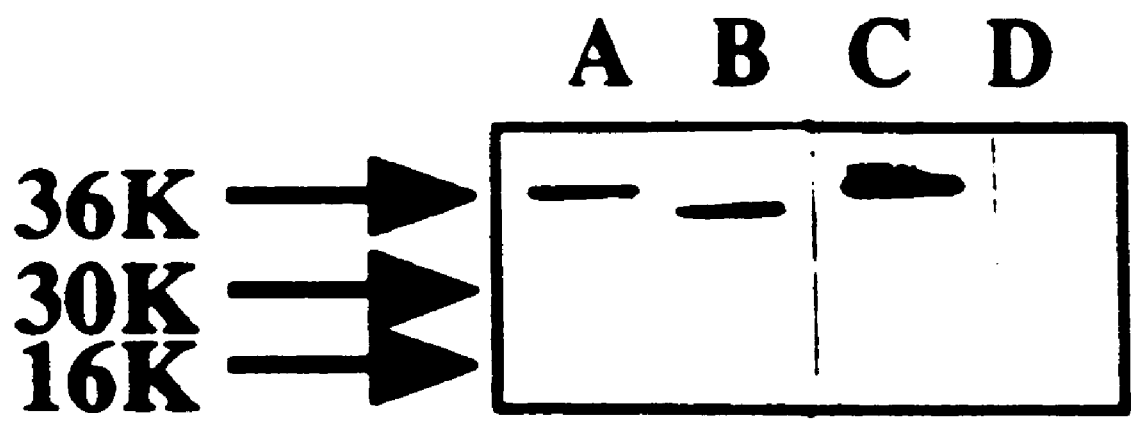
FIG. 2: Sodium dodecyl sulfate polyacrylamide gel electrophoresis of [Sar9,Met(O2)11]-SP-SAP.

FIG. 2 shows electrophoresis of SSP-SAP and SAP by methods described for FIG. 1. In FIG. 2 Lanes A and B are stained with Coomassie staining; lanes C and D are from Western blots using anti-SP. A) SSP-SAP, B) SAP, C) SSP-SAP, D) SSP-SAP under reducing conditions. The migration of SSP-SAP shows a single band with a slight increase in the molecular weight, accounted for by the molecular weight of the 18 amino acid peptide used for the conjugation. No free SAP is evident, nor any evidence of more than one CYGGGGGG-[Sar9,Met(O2)11]-SP (SEQ ID No.3) per molecule of SAP. The Western blotting of the conjugate with an anti-SP antibody indicates that the higher molecular weight species contains SP. The staining is removed upon reduction of the conjugate, indicating that the CYGGGGGG-[Sar9,Met(O2)11]-SP (SEQ ID No. 3) is linked to SAP by a disulfide bond, as planned.

Figure 3:
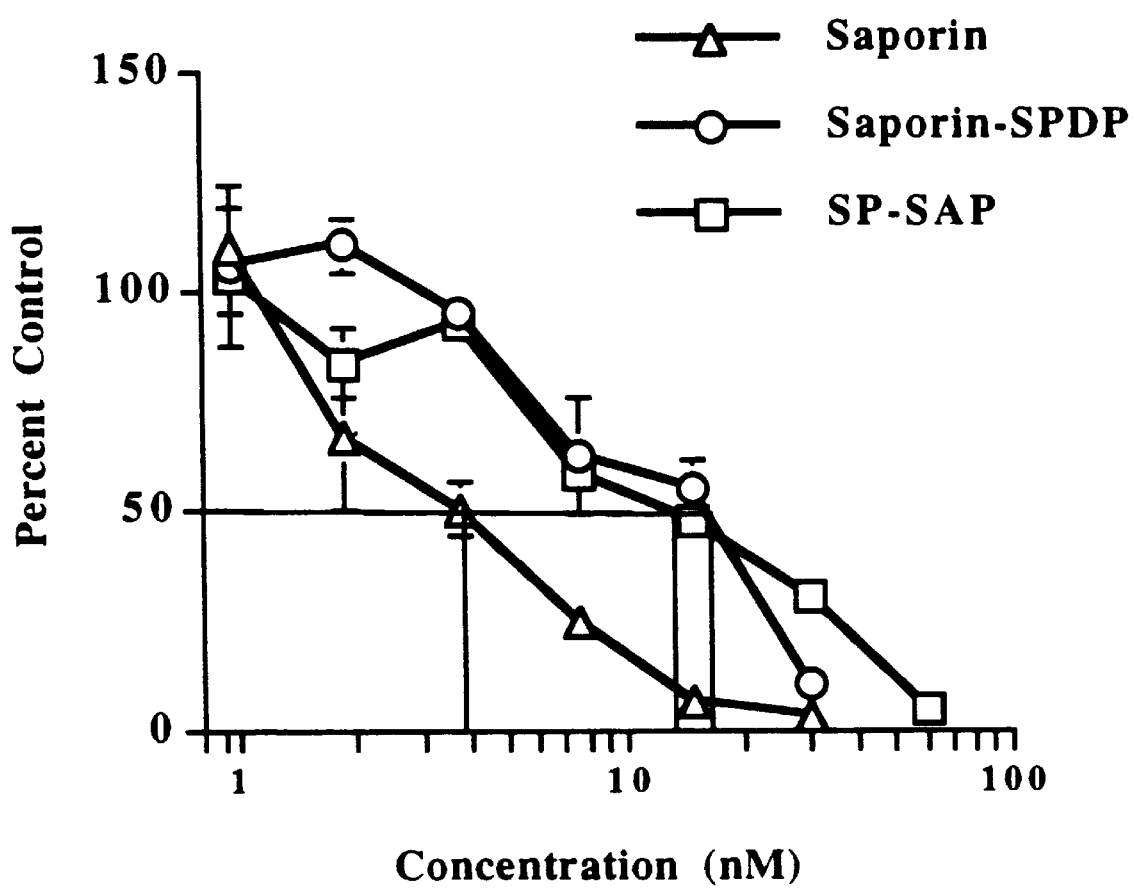
FIG. 3: Protein synthesis inhibition by saporin, derivatized saporin (SAP-SPDP) and NTE-SP-SAP.

SAP activity is measured by inhibition of production of the activity of luciferase by cell-free protein synthesis directed by luciferase mRNA. FIG. 3 shows the results of this assay. This assay shows that SAP in the conjugate retains its protein synthesis inhibition activity, though there is a reduction in activity.

All reagents except samples are purchased from Promega (Madison Wis.). Reaction mixture consisted of 7 ml of rabbit reticulocyte lysate, 20 mM amino acids, 100 ng luciferase mRNA and sample at indicated concentrations in 10 ml volume. Reaction mixture is incubated for 30 minutes at 30° C. Relative light units are measured by Luciferase Assay Reagent in a Berthold Lumat LB9501 luminometer according to manufacturers' instructions.

In this assay, SAP has an ED50 of approximately 4 pM. Comparison with literature values of saporin activity is favorable: reference (23), ED50=30 pM, reference (21) ED50=25 pM. Others (24) have shown that a mutein of SAP, Cys-1SAP, has equal activity to SAP.

Homogenate is prepared and binding performed as previously described (25). Briefly, iodinated SP at 150 pM is incubated in the presence of 100 nM of nonlabeled competitor (NKA: neurokinin A, NKB: neurokinin B). Membrane-bound label is separated from free label by centrifugation and measured with a gamma counter. Control is no addition of competitor.

Figure 4:
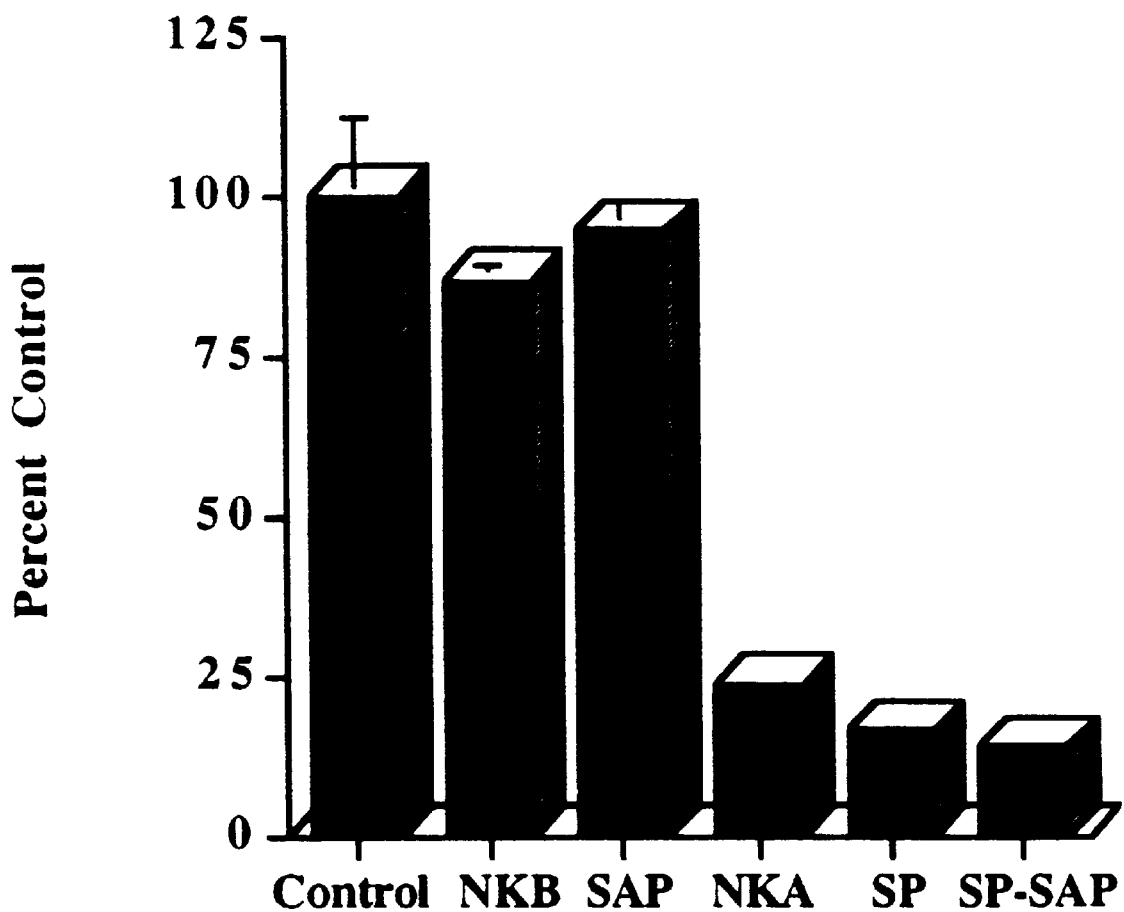
FIG. 4: Inhibition of radiolabeled SP binding to spinal cord membrane homogenates by SP-SAP.

The competitive effect of SP-SAP on SP binding is seen in FIG. 4. The inhibitory effect of the peptide toxin was very similar to that of SP. Binding specificity was shown with controls of SAP and neurokinin B, which showed little or no inhibition of iodinated SP binding (neurokinin A has significant interaction with the NK-1R in this assay). We conclude that SP-SAP retains complete binding to the NK-1 receptor.

Figure 5:
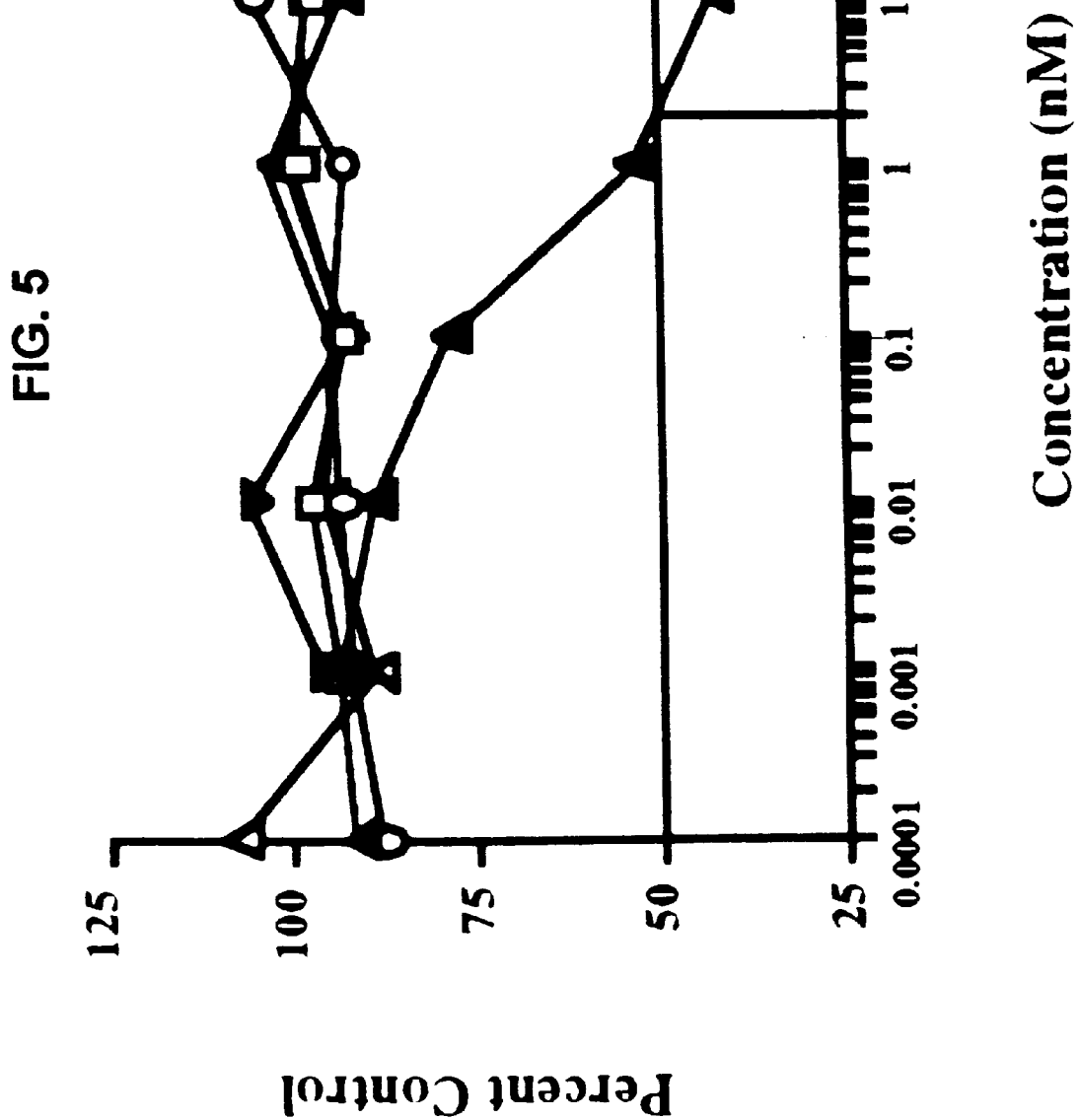
FIG. 5: Cytotoxicity of SP-SAP to KNRK cells and KNRK cells transfected with the NK-1 receptor.

Cytotoxicity Assay: Dr. Nigel Bunnett provided KNRK cells that have been transfected with the rat NK-1 receptor (26). These cells express approximately 80,000 receptors which bind SP with a Kd of 6 nM (27). SP is internalized by the receptor in these cells. The cells appear to have many qualities to be a candidate for a cytotoxicity assay. We tested SP-SAP against these cells and against KNRK cells that have not been transfected and that do not express the receptor. When challenged with SP-SAP, cytotoxicity is seen in a dose-dependent manner in the transfected cells; no cytotoxicity is seen at the same levels with the non-transfected cells (FIG. 5). The data reveals the potency of targeting SAP with substance P. Because SAP has no method of internalization, it has a rather weak ED50 of about 1 mM. Entrance to these cells by SAP is probably due to bulk-phase endocytosis. When targeted with substance P, SAP becomes approximately 500-fold more toxic (ED50 of about 2 nM) to the target cells, while maintaining low toxicity to non-target cells.

Cells, either KNRK cells transfected with the NK-1 receptor (27), or non-transfected KNRK cells (American Type Culture Collection, Rockville, Md.) were plated at 2500 cells per 90 ml in triplicate in wells of a 96 well plate. Cells were allowed to attach overnight and then samples were added at the indicated concentrations and incubated for 48 hours. MTS (Promega, Madison, Wis.) and phenazine methosulfate (Sigma) were added according to distributor's (Promega) instructions and incubated for one hour. Optical density was measured at 490 nm and compared to standard wells with addition of phosphate-buffered saline. In the case of inhibition studies with anti-SP, anti-SP was preincubated with SP-SAP for 30 minutes before addition to cells. Standard deviation for all points was less than 10%. Additions are: to transfected cells: SP-SAP; SAP; SP; an equimolar mixture of SP and SAP. FIG. 5 shows SP-SAP addition to non-transfected KNRK cells.

KNRK cells transfected with the NK-1 receptor were challenged as described in FIG. 5. As show in FIG. 6 lane A: no addition control; B: 1 nM SP-SAP; C-G contain 1 nM SP-SAP. C: 0.1 ml anti-SP; D: 1 ml anti-SP; E: 0.1 mM SPa; F: 1 mM SPa. In G, SP-SAP was pre-incubated with 5 mM dithiothreitol for thirty minutes and then diluted for assay at 1 nM. In the case of competitive inhibition studies with peptide, peptide was added 30 minutes before SP-SAP. SPa is an N-terminal-extended analog of [Sar9, Met(O2)11-SP (18).

Figure 6:
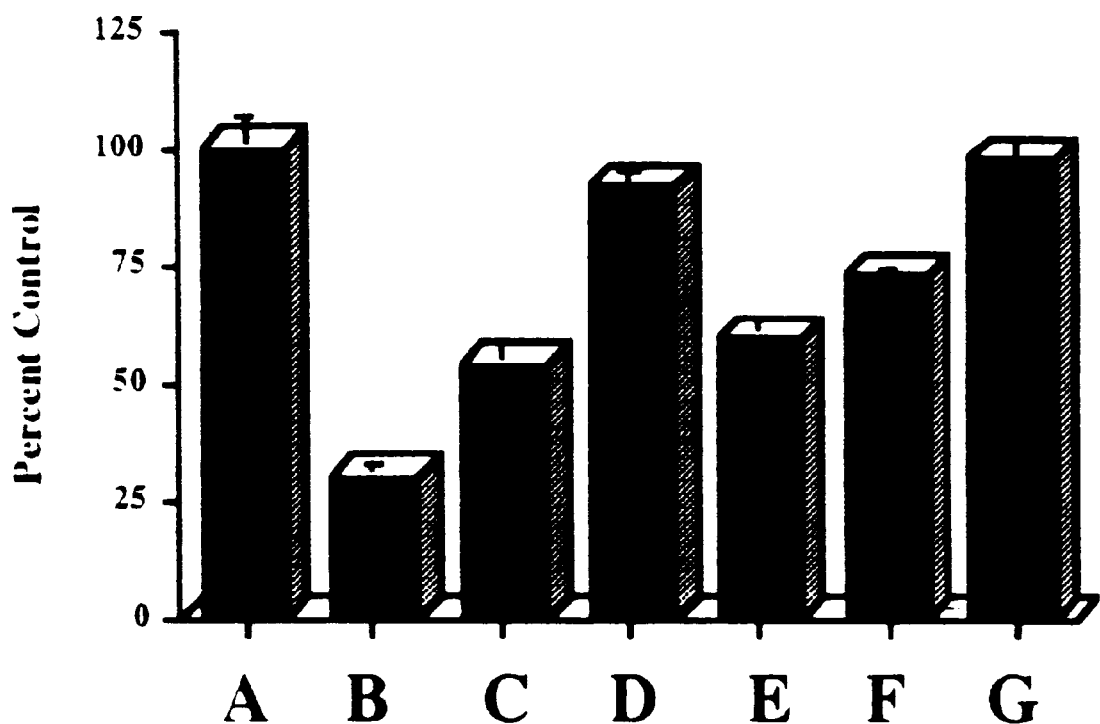
FIG. 6: Inhibition of SP-SAP demonstrates that cytotoxicity is mediated by SP.

Further evidence that the cytotoxicity is mediated by SP is provided by more experiments with the NK-1-R-bearing cells, seen in FIG. 6. Polyclonal rabbit anti-serum to SP inhibits, in a dose-dependent manner, the cytotoxicity of SP-SAP (FIG. 6C,D), presumably by interfering with the ability of SP to bind to its receptor. Excess agonist of substance P is also able to inhibit the cytotoxicity in a dose-dependent manner (FIG. 6E,F). Finally, pretreatment of SP-SAP with a reducing agent, which will break the covalent bond between SP and SAP, completely eliminates the cytotoxicity. These data are powerful demonstrations that the cytotoxicity of SP-SAP is mediated through the binding and internalization of SP and the conjugated SAP by the NK-1R.

Figure 7:
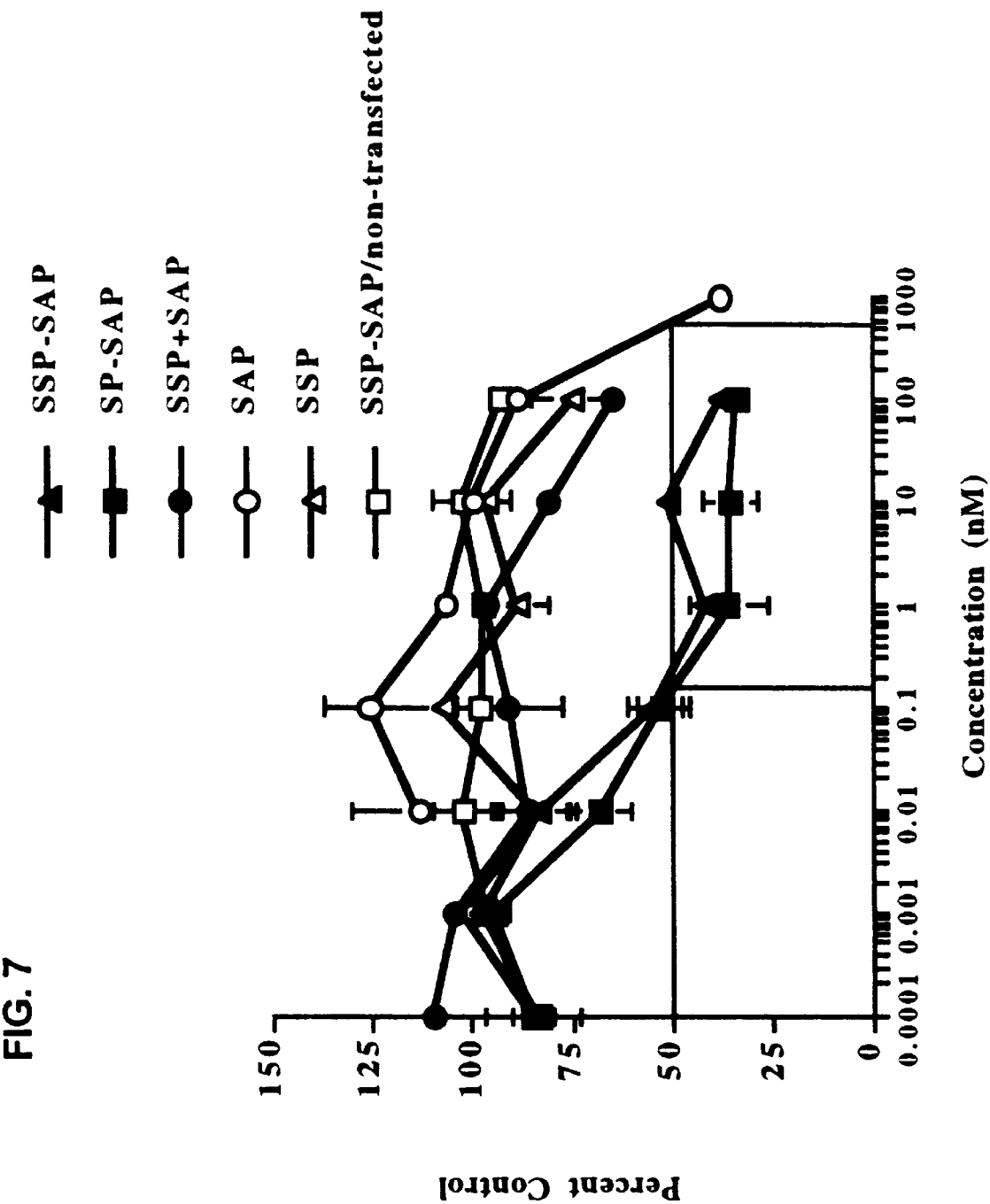
FIG. 7: Cytotoxicity of Stable SP-SAP to KNRK cells transfected with the NK-1 receptor.

The cytotoxicity of [Sar9,Met(O2)11]-SP-SAP to cells that express the NK-1 receptor have been examined. Methods are the same for FIG. 5. The results are seen in FIG. 7. SSP-SAP has similar cytotoxicity to NK-1R-expressing cells as SP-SAP. It has no effect on cells that do not express NK-1R. MTS (Promega) was added according to manufacturer's is instructions for one hour and absorbance at 490 nm was recorded and normalized to untreated control well values.

In vivo data has been obtained that shows the proposed construct, SSP-SAP, is more active in vivo than SP-SAP, both after striatal and spinal intrathecal injections. Observations of rats with spinal intrathecal injections of SSP-SAP show reduced sensitivity to painful stimuli.

FIG. 9 shows a recombinant form of saporin and substance P expressed in a recombinant protein expression system with the sequence of saporin, an appropriate linker and substance P that terminates with an additional glycine after Met$^{11}$. The purified expressed protein is then converted to the amide with an appropriate enzyme, e.g. peptidylglycine-a-amidating monooxygenase.

FIG. 9A is the actual procedure for the synthesis of SP-SAP. SP is Substance P, a peptide with the sequence: RPKPWWFFGLM-amide (SEQ ID No: 4). 1 is the ribosome-inactivating protein saporin, from either the native source, Saponoria officinalis, or the recombinant form, derivatized with a reagent that introduces a sulthydryl group such as 2-iminothiolane or pyridyldithio-propionate. FIG. 9B is the actual procedure for the synthesis of [Sar$^9$, M(O$_2$)$^{11}$]SP-SAP. [Sar$^9$,M(O$_2$)$^{11}$], substance P with the amino acid sarcosine at position 9 and methionine at position 11. FIGS. 9C, 9D and 9E are methods for the synthesis of SP-SAP or [Sar$^9$, M(O$_2$)$^{11}$] SP-SAP. 2 is the recombinant saporin with a cysteine incorporated into the sequence.

1. Striatal injections

Five adult, male Sprague-Dawley rats were pressure microinjected with SSP-SAP into the striatum. All rats were observed for open field ambulation; no consistent changes were observed after immunotoxin injection. Four rats were sacrificed and brain sections processed to analyze the effects of SSP-SAP on striatal neurons. In all 4 rats, there was significant loss of neurons staining immunohistochemically for the NK-1 receptor. In the 2 rats injected with 4.35 ng of SSP-SAP, >90% of the striatal area in frontal sections through the injection site was devoid of NK-1R+ neurons. In one of the rats injected with 2.17 ng, the area devoid of NK-1R was 70–80% of the striatal area at the level of the injection site, but in the other rat, the injection site was medial and affected only the medial half of the striatum. In all 3 rats with accurate injections, the region of loss of NK-1R staining extended throughout the rostral-caudal extent of the striatum.

Neurons staining for choline acetyltransferase also were undetectable in the same region as that in which the NK-1R stain was absent. In sharp contrast, neurons stained for parvalbumin were present in abundance throughout the striata of injected rats. Indeed, neurons stained for parvalbumin could be seen within a few μm of the injection track. Cresyl violet stained sections showed good preservation of normal striatal architecture. The only consistent lesion seen in cresyl violet stained sections was the damage from the pipette track. These findings are illustrated in panels C and D of the attached figure. These results with SSP-SAP injections into the striatum show that SSP-SAP is active in vivo and more selectively toxic to neurons expressing NK-1R than SP-SAP because the size of the region devoid of NK-1R stain is several-fold larger than with SP-SAP while nonspecific tissue damage is confined to the track of the injection pipette. 2.6 ng of SP-SAP injected into the striatum affected less than 50% of the striatal area at the level of the injection site. Higher doses of SP-SAP produced evidence of nonspecific tissue damage. Presumably, the superiority of SSP-SAP over SP-SAP is due to the somewhat higher affinity of SSP-SAP for the NK-1R and the greater stability of SSP compared to SP in vivo.

These data indicate that SSP-SAP may be useful to eliminate NK-1R expressing neurons located deeper in the dorsal horn. Thus it may be useful to cause complete loss of pain sensation. SP-SAP may be more useful for elimination of lamina 1 neurons of the dorsal horn and concomitant elimination of hyperalgesic pain. Both compounds may be useful in the elimination of acute hyperalgesic pain, depending on the dosage.

2. Lumbar intrathecal injections

Three rats were pressure microinjected with SSP-SAP into the lumbar subarachnoid space. Two rats received 870 ng and one rat received 1.3 micrograms. Over the next week, these rats developed insensitivity to painful stimuli applied to their tails and hindpaws including heat (tailflick) and pinching. Two rats (one with 870 ng and the one with 1.3 micrograms) developed partial paralysis of one hindlimb. The third rat (870 ng) showed no motor abnormality but had the same sensory deficits. After two weeks, the rats were injected with formalin into the fully mobile hindpaw. They were injected in pairs with normal rats and observed for 90 minutes. The normal rats showed typical responses to the formalin injection including limping, guarding, licking and biting the injected paw. The SSP-SAP rats showed almost no such response to formalin. One rat (1.3 μg) showed very infrequent guarding and licking after 60 minutes at the time when control rats showed vigorous pain behavior. Spinal cords were processed for detection of NK-1R and showed decreased staining in the dorsal horn (see panels A and B of FIG. 8). Parvalbumin staining, a marker of preservation of neurons that do not express NK-1R, in the dorsal horn was preserved. These results indicate that spinal intrathecal injections of SSP-SAP can be used to lesion NK-1R expressing neurons of the dorsal horn, and suggest that this lesion may decrease pain perception.

FIG. 8 panels A and B are from dorsal horn of the lumbar spinal cord; panels C & D are from the striatum. All sections are stained for demonstration of NK-1R receptor. Panel A shows normal robust staining of the superficial dorsal horn from a normal control rat. Panel B shows loss of this stain in a rat injected with 870 ng of SSP-SAP into the lumbar subarachnoid space. Panel C shows normal NK-1R staining from the striatum contralateral to the SSP-SAP injection shown in panel D. Panel D is from the same rat as panel C and shows complete loss of NK-1R staining in the striatum after injection of 4.35 ng of SSP-SAP. The arrowheads indicate the injection track. Magnification bar in panel B indicates 50 ⇥ micrometers and also applies to panel A. Magnification bar in D indicates 100 ⇥ micrometers and also applies to panel C.

Chronic, neuropathic pain: Although the mechanism(s) by which nerve injuries produce chronic pain is not entirely clear, several hypotheses have involved a central role for substance P. Certainly, clinical management and patient responses to treatment of chronic neuropathic pain are very different from acute pain. The models we propose to study involve sciatic nerve transection in midthigh similar to our previous studies of sensory plasticity and sciatic nerve ligation in midthigh. In rats with sciatic transections, suppression of autotomy will be taken to indicate decreased pain. Although there is some dispute about the precise relationship of autotomy to human experience, the current consensus is that it does relate to such clinical problems as phantom limb pain. SP also has been implicated in the development of mechanical allodynia seen with sciatic ligatures. This may reflect the hyperpathia seen in some patients with neuropathic pain.

The findings of this experiment are of great importance to any possible therapeutic use of SSP-SAP in patients who have neuropathic pain, a common clinical situation. Our hypothesis is that destruction of lamina I NK-1R+ neurons will diminish autotomy by preventing rostral propagation of inappropriate neural activity.

The fornalin test has made important contributions to the battery of tests used in basic pain research. It is considered to be one of the standard animal models of nociception that occurs in humans.

In conclusion, results here indicate that SP-SAP and SSP-SAP are important agents in the control of chronic pain. Many types of chronic pain are now untreatable or intractable.

References

1. Immunohistochemical localization of substance P receptor in the central nervous system of the adult rat. J. Comp. Neurol. 347:249–274.
2. Brown, J. L., H. Liu, J. E. Maggio, S. R. Vigna, P. W. Mantyh, and A. I. Basbaum. 1995. Morphological characterizatidn of substance P receptor-immunoreactive neurons in the rat spinal cord and trigeminal nucleus caudalis. J. Comp. Neurol. 356:327–344.

3. Picard, P., D. Regoli, and R. Couture. 1994. Cardiovascular and behavioral effects of centrally administered tachykinins in the art: characterization of receptors with selective antagonists. Br. J. Pharmacol. 112:240–249.

4. Humpel, C. and A. Saria. 1993. Intranigral injection of selective neurokinin-1 and neurokinin-3 but not neurokinin-2 receptor agonists biphasically modulate striatal dopamine metabolism but not striatal preprotachykinin-A mRNA in the rat. Neurosci. Lett. 157:223–226.

5. Guzman, R. G., K. M. Kendrick, and P. C. Emson. 1993. Effect of substance P on acetylcholine and dopamine release in the rat striatum: a microdialysis study. Brain Research 622:147–154.

6. Anderson, J. J., S. Kuo, T. N. Chase, and T. M. Engber. 1994. Dopamine D1 receptor-stimulated release of acetylcholine in rat striatum is mediated indirectly by activation of striatal neurokininl receptors. J. Pharmacol. Exp. Therap. 269:1144–1151.

7. Yashpal, K., G. M. Pitcher, and J. 1. Henry. 1995. Noxious peripheral stimulation produces antinociception mediated via substance P and opioid mechanisms in the rat tail-flick test. Brain Res. 674:97–103.

8. Neugebauer, V., H. G. Schaible, F. Weiretter, and U. Freudenberger. 1994. The involvement of substance P and neurokinin-1 receptors in the responses of rat dorsal horn neurons to noxious but not to innocuous mechanical stimuli applied to the knee joint. Brain Res. 666:207–215.

9. Chapman, V. and A. H. Dickenson. 1993. The effect of intrathecal administration of RP67580, a potent neurokinin 1 antagonist on nociceptive transmission in the rat spinal cord. Neurosci. Lett. 157:149–152.

10. McCarson, K. E. and J. E. Krause. 1995. The formalin-induced expression of tachykinin peptide and neurokinin receptor message RNAs in rat sensory ganglia and spinal cord is mediated by opiate preadministration. Neuroscience 64:729–739.

11. Luo, L. and Z. Wiesenfeld-Hallim. 1995. The effects of pretreatment with tachykinin antagonists and galanin on the development of spinal cord hyperexcitability following sciatic nerve section in the rat. Neuropeptides 28: 161–166.

12. Yashpal, K., S. Kar, R. Quirion, C. W. Hui-Chan, and J. 1. Henry. 1995. Noxious stimulation decreases substance P binding in rat spinal dorsal horn: competition by endogenous ligand? NeuroReport 5:2101–2104.

13. Sann, H., G. Jansco, W. Rossler, and F. K. Pierau. 1995. Reduction of substance P binding sites in the spinal dorsal horn after perineural capsaicin treatment in the rat. Neurosci. Lett. 190:151–154.

14. Kar, S., R. G. Rees, and R. Quirion. 1994. Altered calcitonin gene-related peptide, substance P and enkephalin immunoreactivities and receptor binding sites in the dorsal spinal cord of the polyarthritic rat. Eur. J. Neurosci. 6:345–354.

15. Smith, G., S. Harrison, J. Bowers, J. Wiseman, and P. Birch. 1994. Non-specific effects of the tachykinin NK1 receptor antagonist, CP-99,994, in antinociceptive tests in rat, mouse and gerbil. Eur. J. Pharmacol. 271:481–487.

16. Neugebauer, V., F. Weiretter, and H. G. Schaible. 1995. Involvement of substance P receptors in the hyperexcitability of dorsal horn neurons during the development of acute arthritis in rat's knee joint. J. Neurophysiol. 73:1574–1583.

17. Tadano, T., T. Asao, T. Aizawa, S. Sakurada, Y. Abe, A. Yonezawa, R. Ando, Y. Arai, H. Kinemuchi, and K. Kisara. 1995. Immunohistochemical determination of rat spinal cord substance P, and antinociceptive effect during development of thiamine deficiency. Brain Res. 696:21–29.

18. Anton, P. A., Jr Reeve, J. R., A. Vidrich, E. Mayer, and S. Shanahan. 1991. Development of a biotinylated analog of substance P for use as a receptor probe. Laboratory Investigation 64:703–708.

19. Lambert, J. M., P. D. Senter, A. Yau-Young, W. A. Blattler, and V. S. Goldmacher. 1985. Purified immunotoxins that are reactive with human lymphoid cells. J. Biol. Chem. 260:12035–12041.

20. Lappi, D. A., R. Matsunami, D. Martineau, and A. Baird. 1993. Reducing the heterogeneity of chemically conjugated targeted toxins: homogeneous basic FGF-saporin. Analytical Biochemistry 212:446–451.

21. Lappi, D. A., D. Martineau, P. Sarmientos, L. Garofano, A. P. Aranda, A. Miyajima, T. Kitamura, and A. Baird. 1993. Characterization of a saporin mitotoxin specifically cytotoxic to cells bearing the granulocyte-macrophage colony-stimulating factor. Growth Factors 9:31–39.

22. Lappi, D. A., F. S. Esch, L. Barbieri, F. Stirpe, and M. Soria. 1985. Characterization of a Saponaria officinalis seed ribosome-inactivating protein: immunoreactivity and sequence homologies. Biochem. Biophys. Res. Commun. 129:934–942.

23. Lappi, D. A., D. Martineau, and A. Baird. 1989. Biological and chemical characterization of basic FGF-saporin mitotoxin. Biochem. Biophys. Res. Commun. 160:917–923.

24. Buechler, Y. J., B. A. Sosnowski, B. A. Victor, Z. Parandoosh, S. J. Bussell, C. Shen, M. Ryder, and L. L. Houston. 1995. Synthesis and characterization of a homogeneous chemical conjugate between basic fibroblast growth factor and saporin. Eur. J. Biochem. 234:706–713.

25. Mantyh, P. W., C. J. Allen, S. D. Rogers, E. DeMaster, J. R. Ghilardi, T. Mosconi, L. Kruger, P. J. Mannon, I. L. Taylor, and S. R. Vigna. 1994. Some sensory neurons express neuropeptide Y receptors: potential paracrine inhibition of primary afferent nociceptors following peripheral nerve injury. J. Neurosci. 14:3958–3968.

26. Vigna, S. R., J. J. Bowden, D. M. McDonald, J. Fisher, A. Okamoto, D. C. McVey, D. G. Payan, and N. W. Bunnett. 1994. Characterization of antibodies to the rat substance P (NK-1) receptor and to a chimeric substance P receptor expressed in mammalian cells. J. Neurosci. 14:834–845.

27. Grady, E. F., A. M. Garland, P. D. Gamp, M. Lovett, D. G. Payan, and N. W. Bunnett. 1995. Delineation of the endocytotic pathway of substance P and its seven-transmembrane domain NK1 receptor. Mol. Biol. Cell 6:509–524.

28. Tjølsen A, Berge O-G, Hunskaar S, Rosland J H Hole K. 1992. The formalin test: an evaluation of the method. Pain 51:5–17, 1992

What is claimed is:

1. A conjugate comprising Substance P or an analog thereof, which analog is selected from the group consisting of GYGGGGGGGKPKPQQFFSarLMet($O_2$)-amide (SEQ ID No.:1) and GYGGGGGGGRPKPQQFFGLM-amide (SEQ ID No.:2), and Saporin.

2. The conjugate of claim 1, wherein the conjugate comprises an analog of Substance P which is an amino acid sequence CYGGGGGGGRPKPQQFFSarLMet ($O_2$)-amide (SEQ ID No. 1).

3. The conjugate of claim 1, where the conjugate comprises an analog of Substance P which is an amino acid sequence CYGGGGGGGRPKPQQFFGLM-amide (SEQ ID No. 2).

4. A conjugate comprising Substance P and a ribosome-inactivating protein.

5. The conjugate of claim 4, wherein the ribosome-inactivating protein is ricin A chain, gelonin, pokeweed antiviral protein, diphtheria toxin or pseudomonas aeruginosa toxin.

6. A pharmaceutical composition comprising a therapeutically effective amount of the conjugate of claim 1 and a pharmaceutically acceptable carrier.

7. A pharmaceutical composition comprising a therapeutically effective amount of the conjugate of claim 3 and a pharmaceutically acceptable carrier.

8. A pharmaceutical composition comprising a therapeutically effective amount of the conjugate of claim 3 and a pharmaceutically acceptable carrier.

9. A pharmaceutical composition comprising a therapeutically effective amount of the conjugate of claim 4 and a pharmaceutically acceptable carrier.

* * * * *

UNITED STATES PATENT AND TRADEMARK OFFICE
CERTIFICATE OF CORRECTION

PATENT NO. : 6,063,758
DATED : May 16, 2000
INVENTOR(S) : Douglas A. Lappi and Ronald G. Wiley It is certified that error appears in the above-identified patent and that said Letters Patent is hereby corrected as shown below:

Claim 1,
Lines 3-4, the sequence "GYGGGGGGGKPKPQQFF Sar L Met ($O_2$) - amide (SEQ ID No.: 1)" should read -- CYGGGGGGGRPKPQQFF Sar L Met ($O_2$) - amide (SEQ ID No.: 1) --
Lines 4-5, the sequence "GYGGGGGGGRPKPQQFFGLM - amide (SEQ ID No. 2)" should read -- CYGGGGGGGRPKPQQFFGLM - amide (SEQ ID No. 2) --

Signed and Sealed this

Second Day of April, 2002

Attest:

JAMES E. ROGAN
Attesting Officer        Director of the United States Patent and Trademark Office

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
       (A) LENGTH: 17 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:1:

Cys Tyr Gly Gly Gly Gly Gly Gly Arg Pro Lys Pro Gln Gln Phe
1               5                   10                  15

Phe (2) INFORMATION FOR SEQ ID NO:2:

(i) SEQUENCE CHARACTERISTICS:
       (A) LENGTH: 20 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:2:

Cys Tyr Gly Gly Gly Gly Gly Gly Arg Pro Lys Pro Gln Gln Phe
1               5                   10                  15

Phe Gly Leu Met
            20

(2) INFORMATION FOR SEQ ID NO:3:

(i) SEQUENCE CHARACTERISTICS:
       (A) LENGTH: 8 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:3:

Cys Tyr Gly Gly Gly Gly Gly Gly
1               5

(2) INFORMATION FOR SEQ ID NO:4:

(i) SEQUENCE CHARACTERISTICS:
       (A) LENGTH: 11 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:4:

Arg Pro Lys Pro Trp Trp Phe Phe Gly Leu Met
1               5                   10